United States Patent [19]

Knüttel et al.

[11] Patent Number: 5,203,339

[45] Date of Patent: Apr. 20, 1993

[54] METHOD AND APPARATUS FOR IMAGING A PHYSICAL PARAMETER IN TURBID MEDIA USING DIFFUSE WAVES

[75] Inventors: Alexander Knüttel, Kensington; Jay R. Knutson, Silver Spring, both of Md.

[73] Assignee: The Government of the United States of America as represented by the Secretary of the Department Health and Human Services, Washington, D.C.

[21] Appl. No.: 722,823

[22] Filed: Jun. 28, 1991

[51] Int. Cl.⁵ .............................................. A61B 5/05
[52] U.S. Cl. .................................... 128/665; 356/345
[58] Field of Search ...................... 128/655, 653.1, 664, 128/665; 356/345

[56] References Cited

U.S. PATENT DOCUMENTS

| | | |
|---|---|---|
| 3,400,363 | 9/1968 | Silverman . |
| 3,670,098 | 6/1972 | Korpel . |
| 3,748,470 | 7/1973 | Barrett . |
| 3,831,031 | 8/1974 | Barrett et al. . |
| 3,860,821 | 1/1975 | Barrett . |
| 3,961,191 | 6/1976 | Stoner et al. . |
| 4,146,295 | 3/1979 | Fonrojet et al. . |
| 4,165,462 | 8/1979 | Macovski et al. . |
| 4,277,127 | 7/1981 | Smith et al. . |
| 4,435,838 | 3/1984 | Gourlay . |
| 4,442,455 | 4/1984 | Huignard et al. . |
| 4,767,928 | 8/1988 | Nelson et al. ................ 128/665 X |
| 4,805,627 | 2/1989 | Klingenbeck et al. . |
| 4,860,253 | 8/1989 | Owechko et al. . |
| 4,910,404 | 3/1990 | Cho et al. . |
| 4,948,974 | 8/1990 | Nelson et al. . |
| 5,022,757 | 6/1991 | Modell .......................... 356/349 |
| 5,090,415 | 2/1992 | Yamashita et al. ................ 128/665 |

OTHER PUBLICATIONS

Fishkin et al., "Diffusion of Intensity Modulated Near-Infrared Light in Turbid Media", *Tissues,* SPIE, Los Angeles, California, Jan. 1991.

E. Gratton et al., "A Continuously Variable Frequency Cross-Correlation Phase fluorometer with Picosecond Resolution", vol. 44 *Biophys. J.,* 315-324, Dec. 1983.

*Primary Examiner*—Lee S. Cohen
*Assistant Examiner*—Samuel Gilbert
*Attorney, Agent, or Firm*—Lowe, Price, LeBlanc & Becker

[57] ABSTRACT

Imaging of a turbid object utilizes interference among the modulation wavefronts of a plurality of modulated light rays propagating through the object by diffusion and having predetermined phases relative to one another. A computer controlled phase and amplitude selecting device, such as a zone plate, is used to modulate light rays at appropriate phases in order to obtain constructive interference only at a predetermined portion of the object, including one or more preselected voxels. The rays reflected from (or diffusively transmitted through) the predetermined portion are received simultaneously at a detector, thus providing simultaneously all the data necessary to describe or image the portion. A single detector element may be used to detect the scattered reflected or transmitted light from the portion and to generate a signal representing the amplitude and phase characteristics for the modulation wavefront, thereby to provide absorption (and other) characteristics descriptive of the portion. An array of detectors may be used to detect the light from a plurality of individual voxels simultaneously and to provide such characteristics for each of the voxels. By dynamically controlling the phase and amplitude selecting device, the voxels selected for imaging are changed without mechanical scanning. Light rays having different frequencies may be modulated to provide complete absorption spectra for an arbitrarily selected portion of the object.

21 Claims, 2 Drawing Sheets

METHOD AND APPARATUS FOR IMAGING A PHYSICAL PARAMETER IN TURBID MEDIA USING DIFFUSE WAVES

TECHNICAL FIELD

This invention relates to optical imaging, and more particularly to the use of diffusion characteristics of an object to obtain imaging data describing the internal structure and characteristics of the object upon illumination by phase encoded intensity modulated light beams.

BACKGROUND ART

Numerous techniques and devices are known and available for imaging structures within opaque or turbid objects, such as biological tissue.

For example, X-ray imaging has been widely used to provide shadow images of obstructed structures. Such imaging relies on opacity of dense materials, such as bone structure, relative to surrounding tissue, to attenuate the intensity of X- radiation passing directly through the object to a recording medium, such as photographic film or fluorescent media. The recording medium is exposed to a spatial pattern of radiation corresponding to the intensity of the incident attenuated radiation, thus providing data or shadow image representation of a spatial distribution of internal structural components of differing size and density at different locations in the object being imaged.

In order to obtain a three dimensional view of the imaged object it is necessary to irradiate the object sequentially from all angles, using complex mechanical scanning devices for changing the relative positioning of the source and detector with respect to the imaged object, as with computerized tomography, in order to enable imaging of a single "slice". Other imaging techniques use still other forms of ionizing radiation, such as gamma radiation, to obtain similar results. In addition to these disadvantages, it is necessary to introduce contrast agents into the sample in order to image soft tissue. Such a process adds to the complexity of imaging living subjects.

Similarly, magnetic resonance imaging techniques and ultrasound imaging techniques are known, providing information in the form of images descriptive of the position, size and shape of objects. In NMR (nuclear magnetic resonance) imaging a spatially varying magnetic field is applied to the object while in ultrasound imaging a sonic wave is applied to the object. Mechanical scanning may be necessary for ultrasound imaging in order to apply and to receive the waves to the selected segment to be imaged. Moreover, two dimensional N×N imaging using NMR exploits the frequency domain and the phase domain, and N sequential data acquisitions are required in the phase direction for such imaging. The acquired data detected by an RF pickup coil are then processed to provide an image of the internal structure of the object.

Moreover, there are known techniques for use of light beams for producing an image, wherein one or more light rays travel through an object and the exiting rays are passed through a zone plate to a detector array to provide information relative to the internal structure of the object. Such techniques, however, are subject to significant errors in attempting to image a preselected site. Specifically, resolution is a function of the wavelength. Typical wavelengths for laser generated light are in the range of 0.5 to 1.0 micron. Thus, in order to use a beam of coherent light to image a selected element of an object it is necessary to position the object with extreme accuracy. Positioning errors of less than a micron result in significant errors.

In order to obtain resolution of the order of 1 mm it would be necessary to use electromagnetic radiation having wavelengths in the range of 1 to 10 cm. However, use of this band of frequencies would expose the object to radiation in the microwave region. Such radiation is particularly susceptible to absorption by water in the tissue being imaged. As is known, electromagnetic radiation in the microwave region is thus typically used for heating and cooking. Accordingly, it could be quite harmful to attempt direct optical imaging utilizing electromagnetic radiation having wavelengths appropriate for standard resolution.

Additionally, similarly to X-ray and gamma imaging, known attempts at imaging using rays of partially coherent light rely on shadow-imaging, utilizing only the relatively small number of "prompt" photons which pass directly through the object, in a relatively straight line and with minimal deflection and diffusion. However, a much larger number of photons which pass through the tissue, and which thus potentially carry much more information, are ignored. These are photons which pass through the tissue by the wave diffusion process, hence passing more slowly, at attenuated intensity and undergoing scattering and interference with one another. For various reasons such diffusive rays have been overlooked by the prior art as a source of imaging information.

The theory of propagation of intensity modulated laser beams in turbid media by photon diffusion has been studied and equations have been developed describing wave propagation characteristics. Specifically, attenuation and phase delay of the modulated wavefront have been described in a homogeneous medium, for diffusive waves having a coherent front. The equations were tested for description of photon migration in turbid media, and were used in conjunction with a frequency domain analysis to determine linear scattering and absorption coefficients of a homogeneous, infinite, turbid medium. Fishkin et al., "Diffusion of Intensity Modulated Near-Infrared Light in Turbid Media", *Tissues*, SPIE, Los Angeles, January, 1991.

In a more recent development, it has been proposed to image tissues using intensity-modulated near-infrared light provided by a pulsed laser, using the increased distance of maintained coherence for diffusional waves and the greater depth of propagation for the lower frequency intensity modulation wavefront than for the higher frequency optical field wavefront. Nonetheless, the reported technique has not contemplated a manner in which a particular volume of interest (voxel) at a desired depth may be selected for imaging.

In summary, the known imaging methods and devices suffer from various drawbacks. For example, known techniques do not permit simultaneous imaging of all points of a desired volume of interest within an object. Nor are the known techniques capable of providing information beyond the presence and shape of various structures within an imaged volume. Moreover, where reflectance imaging is used, signals from voxels close to the object surface tend to overwhelm the photodetector, so that selection of deeper voxels is made impractical. Further, various techniques of the prior art require mechanical scanning of an object in order to image a desired voxel, rely on sequential data acquisition, and are incapable of imaging a voxel in real time. Others of the known methods require exposure to ionizing radiation, administration of radioactive contrast or tracing agents, may be invasive in nature, expensive to administer, and suffer from various other deficiencies.

There is accordingly a need for method and apparatus for obtaining data descriptive of characteristics of a turbid medium, and more specifically of tissue, and of its internal structure, which are not subject to the deficiencies of the prior art.

There is a more particular need for a method and apparatus for imaging an object utilizing electromagnetic radiation and permitting resolution in the range of 1 mm, while avoiding use of radiation having wavelengths in the range of 1-10 cm and the harmful effects thereof.

There is a more specific need for a non-invasive method and apparatus for imaging an object, free of requirements for exposure to ionizing radiation and administration of contrast or tracing agents, free of a need for mechanical scanning, and capable of simultaneously providing imaging data representative of a selected volume of interest.

Moreover, there is a need to be able to reflectively image voxels which are deep within the object, without overwhelming the photodetector by signals from voxels close to the surface.

There is still a further need for a method and apparatus for obtaining images or data descriptive of characteristics of a selected voxel of an object by exposure to intensity modulated light beams or other non-ionizing radiation, wherein the acquired images or data are descriptive of characteristics or physical parameters in addition to physical size or presence of structures within the object.

DISCLOSURE OF INVENTION

It is accordingly an object of the present invention to provide a method and apparatus for obtaining data descriptive of characteristics of an object, or for imaging an object, which is a turbid medium, and more specifically of tissue and its internal structure, which are free of the deficiencies of the prior art.

It is a more particular object of the invention to provide a method and apparatus for imaging an object with a resolution in the range of 0.1-1 mm, while utilizing electromagnetic radiation having wavelengths outside the range of 1-10 cm and avoiding the harmful effects thereof.

It is a more specific object of the invention to provide non-invasive method and apparatus for obtaining data descriptive of characteristics of an object, or for imaging an object, which is free of a need for mechanical scanning of the object.

It is still another object of the invention to provide method and apparatus for obtaining data descriptive of characteristics of an object, or for imaging an object, free of requirements for exposure of the object to ionizing radiation and for administration of contrast or tracing agents.

Still another object of the invention is to provide method and apparatus for obtaining data descriptive of characteristics of an object, or for imaging an object which are capable of providing simultaneously imaging data representative of an entire volume in the object.

Yet a further object of the invention is to provide method and apparatus for obtaining data descriptive of characteristics or physical parameters of an object, or for imaging an object, by exposure to intensity modulated light beams or other non-ionizing radiation, wherein the images or data are descriptive of more than mere size or presence of structures within the object.

It is a more specific object of the invention to provide method and apparatus for obtaining simultaneously all data necessary to provide an image of a physical parameter, such as absorption, of a predetermined voxel within an object by interference among the modulation wavefronts of an array of intensity modulated rays, diffusively propagating through the object and provided with a predetermined pattern of phase and amplitude relationships to obtain constructive interference at the predetermined voxel, and for varying the selected voxel by changing the phase pattern thereby to scan non-mechanically the entirety of a volume within the object.

In accordance with these and other objects of the invention, there is provided a method for imaging an object including the steps of applying modulated optical rays at a plurality of points along a surface of the object, the rays each characterized by an amplitude modulated at a respective modulating frequency and by a phase. The phases are provided respective relative phaseshifts selected to cause constructive interference among the modulated rays at a predetermined voxel. Thus, the inventive method effectively selects the predetermined voxel for imaging by selecting the relative phaseshifts for the intensity modulated light rays. In accordance with the method, the modulated rays are diffusively propagated through the object and the intensity and phase of a light ray resulting from the constructive interference at the selected voxel are detected for imaging a characteristic of the voxel.

In order to image a portion of the object which includes a number of objects, the method may include the further steps of repeating the selecting step for a sequence of predetermined voxels, repeating the propagating step to diffusively propagate the modulated rays through the object to the sequence of predetermined voxels, and repeating the detecting step to detect a sequence of rays respectively resulting from a sequence of constructive interferences at the sequence of voxels, thereby scanning a portion of the object for imaging the characteristic thereof. For such a process, the selecting step preferably includes the steps of using a signal responsive phase shift device, such as a zone plate, for applying the relative phaseshifts to the rays. Computer generated signals are applied to the signal responsive phase shift device, thereby providing non-mechanical scanning of the portion of the object to be imaged.

Alternatively, the selecting step may include selection of an arbitrary shape to be imaged by simultaneous, non-sequential application of the modulated phase shifted light rays to a plurality of voxels forming the portion to be imaged. Such an alternate embodiment of the invention includes selecting the relative phaseshifts of the modulated intensities to cause constructive interference among the modulated rays at a predetermined plurality of voxels, thereby selecting for imaging a portion of the object having a predetermined shape formed of the plurality of predetermined voxels. For such a method the detecting step includes detecting light rays resulting from constructive interference at the portion of the object having a predetermined shape.

Where a pattern or other signal responsive zone plate device is used to provide the respective phase shifts to the various rays, constructive interference is caused to occur at the plurality of voxels by using superposition. Thus, a superposition of individual patterns, each of which would produce constructive interference at one voxel, simultaneously provides the desired constructive interference at the plurality of voxels.

Thus, to provide signal responsive constructive interference at a plurality of voxels forming a portion of the object, the selecting step of the inventive method may include the steps of using a signal responsive phase shift device for applying the relative phaseshifts to the rays together with applying a plurality of computer generated signals to the signal responsive phase shift device, thus selecting the predetermined plurality of voxels to form the portion having a predetermined shape for simultaneously illuminating with respective modulated rays the plurality of voxels forming the portion.

To compensate for attenuation of modulation in waves propagating diffusively through a turbid medium, an appropriate distribution of modulation amplitudes is established for the light rays.

In such a plural voxel imaging method, a single detector may be used to detect light rays from the plurality of voxels forming the single portion of the object. Thus, the detecting step of the method includes the steps of: using a single detector cell for detecting intensities and phases of a plurality of light rays from the plurality of voxels, and outputting a signal representative of an image of the portion as a function of the intensities and phases of the plurality of light rays. The function may be an average of the detected intensities and phases of the plural voxels, and may be outputted to represent the absorption characteristic, or image, of the portion of the object. Resolution of such an image may be by imaging individual portions of the object.

With respect to the broad aspects of the invention, a single detector may be used to image, or provide characteristics descriptive of, a single voxel of the object by using a single detector cell for detecting intensity and phase of a light ray from the selected voxel and outputting a signal representative of an image of the voxel as a function of the intensity and phase of the light ray. Further, the optical rays are modulated as part of the inventive method. Particularly, where a signal responsive device is used to provide the selected phase shifts to the various beams, the same or similar device may also be used to modulate the intensity of the optical rays. Thus, the applying step may include the step of using a signal responsive modulating device for modulating the rays with the modulating frequencies and relative phaseshifts. Computer generated signals may be applied to the signal responsive modulating device for selecting predetermined modulating frequencies in accordance with characteristics of the object and for selecting predetermined relative phaseshifts for selecting a predetermined voxel of the object to be imaged.

In accordance with another aspect of the invention, there is provided an improvement for an imaging apparatus which images an object by applying light rays thereto. The improvement provides a parameter detecting device for obtaining physical parameters descriptive of a portion of the object. The parameter detecting device includes a phasing device which provides predetermined phases to modulated light rays applied to the object in order to cause constructive interference between modulation wavefronts at a preselected voxel within the object. Additionally, there is included a detecting device for detecting an amplitude and phase of a diffusively propagated light ray resulting from the constructive interference at the selected voxel, for imaging an absorption characteristic thereof.

The phasing device preferably includes a signal responsive phase shifter, which may be a signal responsive zone plate. Such a zone plate may be formed of an LCD device having a plurality of cells, each cell responsive to a signal for controlling a light transmittance characteristic thereof. Alternatively, the phasing device may include a plurality of signal responsive electro-optic modulators, or other devices, each responsive to a signal for controlling a light transmittance characteristic thereof.

Where a signal responsive phase shifter is used, there is also included a generating device for generating a plurality of signals for controlling the light transmittance characteristics of the elements of the phase shifter in order to provide the predetermined phases to the modulated light rays and to transmit the modulated light rays to the object.

The signal responsive phase shifter may apply a predetermined phase pattern to the light rays for causing constructive interference between the modulation wavefronts at a predetermined plurality of voxels, thus effectively selecting those voxels to form the portion of the object to be imaged. The predetermined phase pattern may be a single pattern or a plurality of patterns. The plurality of patterns may be applied sequentially or may be superposed to provide a single resultant pattern.

The detecting device may include a detector array, which could be constituted of a single detector, for simultaneously receiving a plurality of diffusively propagated light rays resulting from the constructive interference at the selected plurality of voxels, for simultaneously imaging an absorption characteristic or other physical parameter of the plurality of voxels forming the portion of the object being imaged.

Where the phase shifter applies to the light rays a plurality of predetermined phase and amplitude patterns in a predetermined sequence, the constructive interference between the modulation wavefronts occurs at the selected plurality of voxels in a predetermined sequence. Thus, the voxels forming the portion may be scanned non-mechanically by the detector array in the predetermined sequence and the results imaged with a resolution of one voxel.

In accordance with the inventive improvement, there may also be included a modulating device for modulating the light rays at a predetermined modulation frequency, selected to provide a predetermined resolution of the imaged absorption characteristics. As yet another aspect of the invention, the improved imaging apparatus may include a device for applying to the object light rays of a plurality of frequencies, thereby to obtain complete absorption spectra for the selected portion of the object.

BRIEF DESCRIPTION OF THE DRAWINGS

The accompanying drawings, incorporated into and forming a part of the specification, illustrate several aspects of a preferred embodiment of the present invention and, together with the description, serve to explain the principles of the invention. In the drawings.

BEST MODE FOR CARRYING OUT THE INVENTION

Figure 1:
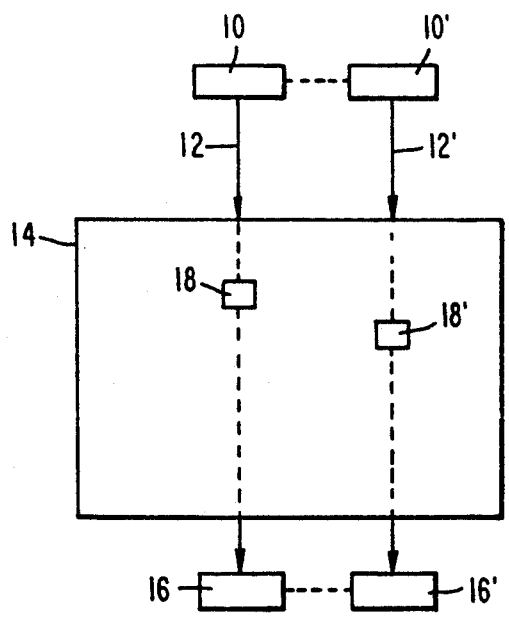
FIG. 1 illustrates a prior art approach to optical imaging of an object.

Referring now to the drawings, there is shown in FIG. 1 a prior art approach to optical imaging of an object. Prior to describing the details of such a prior art approach and of the present improvement thereon, it should be noted that the term optical imaging of an object as used herein relates to detection of a light ray transmitted through, or reflected by, the object of interest and specifically transmitted through or reflected by various internal components of the object. Hereinafter, reference to a light ray received from (or transmitted through) such an element should be understood to include both transmitted and reflected rays. The light ray contains information descriptive of various characteristics of the object or its internal components. For example, the information may be descriptive of the absorption characteristics of the internal structural components of the object, or may be descriptive of density, fluorescence, or other characteristics thereof.

The characteristics of the object may be displayed numerically, or in a one, two or three dimensional plot thereof thereby providing a spatial display of the characteristics of interest, corresponding to the physical structure and location of the various portions of the object which are being imaged. Given the numerical data, the display may be generated electronically, as on a CRT (cathode ray tube) or LCD (liquid crystal display) screen, or by outputting a printed representation thereof.

Further, use of the term "optical" or "light" rays generally refers to electromagnetic radiation, in the visible frequency range of approximately $4 \times 10^{14}$-$8 \times 10^{14}$ Hz with wave lengths in the range of approximately 0.75 to 0.38 micron. However, the present invention is not necessarily limited to the visible spectrum of electromagnetic radiation and other spectra may be utilized, to the extent practicable.

As hereinabove noted, FIG. 1 provides a schematic illustration of a prior art optical imaging approach, wherein a light source 10, which is typically a laser, generates a light ray 12 directed at an object to be imaged 14. After passage through the object, the light ray exits and impinges on a photodetecting device 16, which may be a photomultiplier tube (PMT), a charge coupled device (CCD), or the like. Photodetecting device 16 converts the optical radiation incident thereon to electrical signals in a known manner. The resultant electrical signals are then processed in a well known manner, to obtain numerical data or to generate displays as hereinabove summarized.

Although photodetecting device 16 is shown as receiving the light transmitted through object 14, and is thus on an opposite side of the object from the light source 10, it is also known to provide the photodetecting device 16 on the same side of the object 14 as light source 10, in which case reflected light rays are processed for imaging. Thus, imaging may utilize light rays transmitted through or reflected by the object, and specifically by internal elements 18 within the object being imaged, in order to provide information descriptive of the internal structure of the object. In that regard, it should be appreciated that object 14 is typically a turbid object and that the internal elements 18 are not visible to the unaided eye. However, the object 14 may be of any optical characteristic since the concept of imaging, as hereinabove defined, relates to generation of information characteristic of the internal elements and such information does not necessarily relate to the visibility of the elements.

In a typical prior art imaging attempt, if it is desired to image a number of internal elements of object 14, the light beam 12 must typically be scanned along the object. As shown in FIG. 1, such scanning is typically attained in the prior art by displacement of light source 10 and photodetecting device 16 to alternate positions, as illustrated by 10' and 16' wherein a light ray 12' passes through an internal elements 18'. Alternatively, rather than displacing the light source and photodetecting device, a plurality of light sources and/or a plurality of photodetecting devices may be provided. Typically, a photodetector may include an array of cells, the cells being electronically scanned in a known manner to provide an output voltage for driving a similarly scanned display device.

Such imaging thus provides a "shadow" image wherein directly transmitted light rays impinge on various cells of a photodetector. Where the light rays are obstructed to varying degrees by the internal elements of the object, the cells of the photodetector provide varying output voltages.

Figure 2:
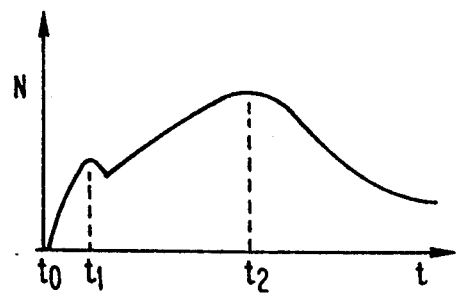
FIG. 2 is a time plot of the number of photons detected by a photodetector in FIG. 1.

The photons passing through object 14, when collected by photodetecting device 16, may be represented by a curve shown in FIG. 2, which illustrates a time plot of the number of photons incident on the device per unit time. Thus, where a laser emits a pulse of coherent light at a time $t_0$, the intensity of received light, represented by the number of photons per unit time N, reaches a peak at time $t_1$, shortly after emission of the pulse. The received peak represents photons passing directly through the object 14 and its internal structure. However, a larger number of photons do not traverse the object in a direct path and, through scattering, are diffused through the object and its internal elements.

The photons detected at time $t_1$ are known in the art as "prompt" photons. It is known, however, that at visible frequencies, a coherent light ray generated by a laser loses its coherence after passing through a very short distance within a turbid object such as biological tissue. Thus, a large number of photons are transmitted diffusively through the object and impinge on the photodetecting device 16 after the detection of the prompt photons. The diffusively transmitted light ray accounts for a glow observed by the photodetecting device 16 represented by a broad peak at time $t_2$ shown in FIG. 2, following the peak detected at time $t_1$. The difference in times $t_1$ and $t_2$ is due to the slower travelling speed of the diffused photons than the prompt photons. In prior art imaging techniques the large number of photons diffusively transmitted (or reflected) by the object are ignored since an optical image is produced using only the small number of prompt photons passing directly through the object.

As hereinabove noted, however, coherence of light rays traveling through the object is lost exponentially in a short distance, dependent on the wave length of the radiation. Since the wave length of light rays is in the order of 0.5μ, it is clear that prior art imaging techniques are ineffective in trying to image turbid objects having a thickness on the order of centimeters. Moreover, if the wave length of the radiation were increased to be in the centimeter range (e.g., 0.1 cm to 10 cm), the radiation would fall in the microwave region of the electromagnetic spectrum. Exposure of living tissue to radiation in that spectrum results in unacceptable heat transfer to the tissue.

Accordingly, in order to overcome these problems, the inventors have provided a method and apparatus wherein the incident light rays are modulated by a modulation signal and the detected diffusively propagated rays are modulated by a signal representing a result of an interference between the modulating signals of the incident light rays. Thus, the incident rays act as carriers for modulation signals having modulation frequencies and longer wave lengths. By providing a modulating signal having a wave length in the range of several centimeters, the radiation travels through the entirety of the object without losing the coherent diffusive nature thereof, thus permitting constructive interference to be established anywhere within the object. Further, the longer wavelengths allow the rays scattered by the imaged portion of the object to propagate to the photodetecting device without loss of coherency, enabling accurate measurement of a phase angle of a detected coherent wave front.

The inventive concept thus permits imaging of objects of significantly greater thickness than permissible by the prior art. Moreover, irrespective of the size of the object being imaged, the method and apparatus described herein utilize the diffusively propagated waves represented by the broad portion of the time plot of FIG. 2.

Although the prior art has observed that the diffused light rays passing through the object are damped and arrive at the photodetector with phase delays caused by the internal structure of the object, the relative phase differences of the diffusively transmitted rays at the surface of the object has not been previously used to select a portion of the object characteristic thereof.

The present invention utilizes the phase variation of a plurality of modulated light rays, provided by one or more light sources in a manner hereinafter described, and the interference between the photon populations of such light rays, to select a volume of interest for imaging. Both the amplitude and phase of the detected resulting diffusively propagated wave fronts may be used to provide information describing the selected volume and any structural elements therein. This concept is illustrated by reference to FIG. 3, which shows the wave fronts associated with two modulated light rays which are simultaneously incident on an object. As shown therein, a first modulated light ray 12 is described by wave fronts indicated at 20 which diffuse through object 14. A second modulated light ray 22 is described by wave fronts 24 diffusing through the object. As is known in the art, the sets of wave fronts 20 and 24 interfere with one another as a function of the phases thereof. Thus, where wave fronts of opposing phases (180° out of phase) intersect, destructive interference occurs and where wave fronts of the same phase (0° or 360° relative phase) intersect, constructive interference takes place. A location wherein destructive interference between unmodulated wave fronts (i.e., "carrier" frequency light rays) occurs is characterized by darkness and a location wherein constructive interference occurs between unmodulated wave fronts is characterized by brightness.

Similar concepts are applicable to interference between modulated wave fronts. However, the interference occurs between the changes in photon densities associated with the modulation of the light wave, rather than between the absolute values of the photon densities associated with the carrier frequency of the light wave. Thus, at specific volume elements of interest, or voxels, constructive and destructive interference among the modulation frequencies of the modulated light rays results in electromagnetic waves having a doubled peak-to-peak modulation amplitude or zero modulation amplitude, rather than darkness and doubled intensity resulting from cancellation of the E field, for example. Of course, where more than two light beams are used, the modulation amplitude resulting from constructive interference is more than double the original amplitudes.

For light rays modulated at less than 100% modulation, there is a d-c background level of illumination intensity at the sites of destructive interference, and a brightened intensity at the points of constructive interference and doubled modulation amplitude. Upon elimination of the d-c background level of illumination, however, the observed interference patterns are the same as those for interfering unmodulated light-rays having a frequency corresponding to the modulation frequency.

By providing appropriate phase shifts to the modulating signals, the location of the points of constructive and destructive interference may be varied so that a particular voxel within object 14 may be selected as a point for constructive interference to occur. The structural element at the selected voxel is thus "illuminated" by a modulated light ray while voxels at the non-selected points adjacent thereto are not. The destructive interference occurring at the non-selected voxels effectively eliminates the modulation signal from the light rays impinging thereon. Accordingly, only the selected voxel acts to scatter a modulated light ray, which thus diffuses through the object and is detected by photodetecting device 16.

Using known techniques from the fields of geometrical optics and optical interference, specific phases are provided to the modulated signals applied to light rays 12 and 22 so that constructive interference will take place at a specific voxel which it is desired to image, as well as at numerous additional voxels. The light ray scattered by that voxel propagates diffusively toward the photodetecting device which produces an output signal having an amplitude and phase corresponding to that of the modulation signal. By providing an entire array of appropriately phased light rays, constructive interference is caused to occur only at a single voxel.

Such phasing may be provided to an array of light beams by application of a pattern known as a Fresnel zone plate. Superposition of a plurality of such patterns results in constructive interference at the plurality of voxels which would individually be selected for constructive interference by the individual patterns. Thus, any selected portion of object 14 may be imaged by superposing a plurality of patterns which individually cause constructive interference only in the individual voxels making up the desired portion.

Such a process effectively steers a modulated light ray to illuminate a selected portion of an object and corresponds to beam steering techniques utilized in phased-array radar systems, the details of which are well known and need not be duplicated herein. However, specific illustrative examples are provided below to demonstrate the novel manner in which the technique is applied in accordance with the invention. As hereinabove noted, once such constructive interference has been established, i.e., once a voxel at a desired location within the object 14 has been illuminated by the modulated light rays 12 and 22, the voxel (or internal element of object 14) acts as a source of radiation, as shown in FIG. 4.

Figure 3:
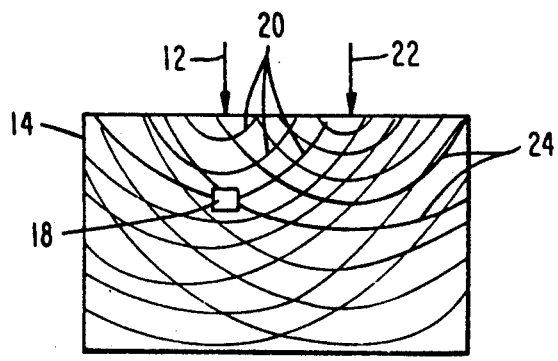
FIG. 3 shows the wavefronts associated with two light rays incident on an object to be imaged.
Figure 4:
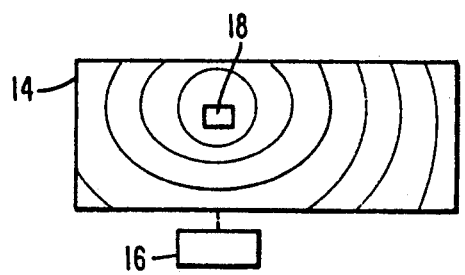
FIG. 4 illustrates results of constructive interference occurring in the arrangement of FIG. 3.

Referring now to FIG. 4, the results of constructive interference between the two light rays 12 and 22 in FIG. 3 are shown as a series of wave fronts emanating from the portion 18 (or from the specific voxel) wherein constructive interference takes place. Referring to the voxel as an internal structural element 18 of the object 14, it is seen that a series of wave fronts of the modulated illuminating light emanate from the voxel and diffuse throughout the object. The diffusive wave fronts are detected at photodetecting device 16 and have a particular phase dependent on the path length from voxel 18 to the detecting device 16. By measuring the amplitude and phase angle of the detected wave fronts, the characteristics of any structural element which may be located at voxel 18 may be detected.

For example, it is known that the amplitude of the peak to peak voltage output by the photodetecting device 16 is inversely proportional to the absorption coefficient. Accordingly, by beam-steering a plurality of modulated light rays to various voxels within the object, a plot of the inverse of the detected peak-to-peak amplitude reveals an absorption characteristic for the voxels. Thus, an absorption characteristic for an arbitrarily shaped volume of the object is obtained by application of appropriate phases to a plurality of light rays in order to cause constructive interference only at various voxels within the volume, and by plotting the inverse of the detected peak-to-peak voltage, thus providing an absorption image of the volume. Further, by performing the above noted procedure for modulated light rays of a plurality of optical frequencies, complete absorption spectra may be obtained for each of the voxels in the desired volume within the object.

Such absorption spectra are obtained for any arbitrarily shaped portion of the object by providing appropriate phase and amplitude patterns for the light rays of different frequencies. Towards that end, the light source used to provide the light rays may be a mode locked laser which produces a frequency comb of modulation frequencies. Thus, by manipulating the output radiation of such a mode locked laser, an absorption image may be obtained for any arbitrarily shaped volume or other portion of interest within an object, showing absorption spectra for each voxel within the portion. Such a technique provides a marked advance in the art of imaging, by enabling non-invasive measurement and imaging of the precise chemical composition of any point within a body.

Additional information descriptive of optical density, fluorescence, and other characteristics of the object may be obtained from the relative phases of the detected light rays. For example, a physical experiment of fluorescence using phase data is described in "A Continuously Variable Frequency Cross-Correlation Phase Fluorometer With Picosecond Resolution", E. Gratton et al., 44 *Biophys. J.* 315-324, Dec., 1983.

From the foregoing it is clear that a very significant aspect of the invention is the ability to image a number of characteristics of any arbitrary voxel, at arbitrary depth and location within the object. As has been emphasized, such volume selection is attained by establishing a condition of constructive interference at the selected voxel. A straight forward method for providing such interference may be obtained from classical optical theory used for coherent electromagnetic waves, as exemplified by Fresnel zone plates.

Figure 5:
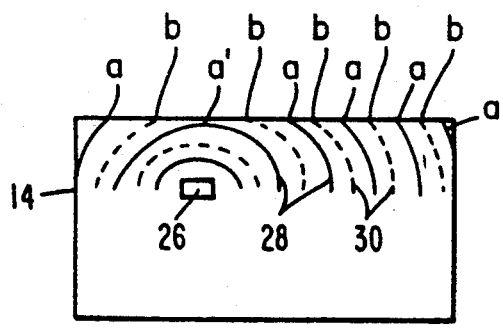
FIG. 5 shows a principle of the method used to implement phase steering in accordance with the invention.

FIG. 5 shows such a technique as applied to cause the desired constructive interference in an object to be imaged in accordance with the invention. Referring to the Figure, wavefronts are drawn which would emanate from the voxel 26 at the particular frequency of the light ray as modulated by the modulation signal, with due consideration of the reduction in wavelength caused by propagation through the medium of the object 14. Thus, similarly to obtaining a Fresnel zone plate for phases of the unmodulated light rays of a particular frequency, there are drawn wavefronts corresponding to the phases of the modulation signal, rather than to the phases of the optical light ray itself. In FIG. 5, wave fronts 28 correspond to maxima of the modulation signal and wave fronts 30, shown in dashed line, correspond to points one half wavelength out of phase with the fronts 28, i.e, to minima of the modulation signal.

By analogy with standard optical considerations, application of coherent modulated light rays having a phase corresponding to a maximum modulation signal to points a along the surface, along with application to points b of modulated light rays half wavelength out of phase therewith i.e., of minimal modulation signal, will result in constructive interference at the location of voxel 26. A top view of the surface of the object to be imaged is shown in FIG. 6, wherein the resultant "zone plate" to be applied to the surface is shown as the well known bull's eye phase pattern 32.

As is known from the field of optics, the principle of superposition applies so that, in order to obtain constructive interference at two voxels the separate phase patterns for each may be superimposed on one another and coherent modulated light rays applied through the resulting pattern.

Figure 6:
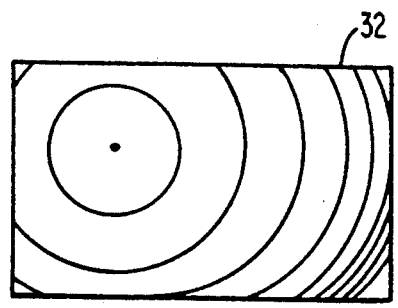
FIG. 6 shows a top view of a zone plate applied to the object shown in FIG. 5.

A number of techniques may be used to provide a phased array of coherent modulated light rays for application to the surface of object 14 in accordance with the pattern of FIG. 6. In each case, the phase pattern is represented by a two dimensional array of pixels, each of which provides for the incoming light beam a phase established by the desired phase pattern. In some embodiments, the pixels may also modulate the incoming light by the modulation frequency selected for proper penetration of the object and resolution of the image. In its simplest form, there may be provided a structure blocking light transmission everywhere but at the points of peak amplitude, corresponding to points a in FIG. 5, and in conformity with the illustration of FIG. 6. Of course, such a device may be electronically implemented, under computer control, as follows.

In principle, oscillating signals (which may be generated by a computer) are applied to the array of pixels, thus causing the pixels to alternate between transmitting and blocking of light passing therethrough. The signals applied to pixels along the rings are all controlled to oscillate in phase at the desired modulating frequency, e.g. 1 GHz. The signals applied to pixels in the open areas between the rings may be controlled to oscillate at the same frequency, with a phase shift of 180 degrees relative to the signals applied to the pixels along the rings. Thus, the transmissivities of the pixels along the rings and therebetween are 180 out of phase, so that coherent light applied to the pixels is modulated in accordance with the pattern of FIG. 6, and constructive interference is established at the desired volume of interest.

Provision of timed signals by a computer is well known. Thus, a computer is easily programmed to excite an appropriate device, as hereinbelow described, to produce an image as shown in FIG. 6 wherein the signals provided to various groups of pixels are at predetermined phase relationships relative to one another. Accordingly, a computer controlled zone plate is provided for selection of an arbitrary voxel to be imaged. Where the array of pixels is used only to provide the phase determinative pattern of FIG. 6, without also modulating the light rays, modulation may be performed prior to application of the light rays to the computer driven zone plate, which then is required only to provide the desired phase distribution to the light rays passing therethrough.

In a departure from classical optics, it should be recognized that the degree of modulation intensity of the coherent beams is damped exponentially when passing through tissue. Such damping is easily compensated for by varying the amplitude of the modulating signal applied to the modulators in the above described embodiment. Specifically, the amplitude of the modulation signal is made exponentially inversely proportional to the distance between the pixel and the voxel to be imaged, thus resulting in a uniform intensity of the modulated light rays reaching the voxel and assuring that constructive interference occurs therebetween. For the pattern of FIG. 6, it will be recognized that the modulation amplitude is the same for all pixels on a given ring.

Figure 7:
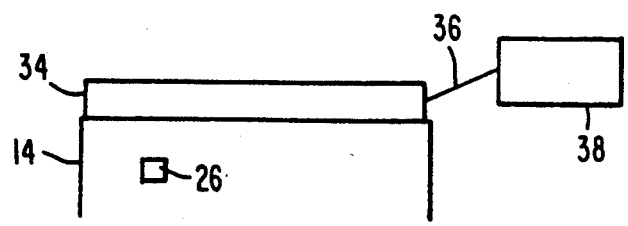
FIG. 7 shows one embodiment of an imaging device in accordance with the invention.

In one embodiment, shown in FIG. 7, a liquid crystal display (LCD) 34 is used to implement the zone plate, in which control signals 36 are provided by a computer 38 for generating each pixel of an image. For imaging a single voxel 26, the image generated on the display corresponds to the pattern shown in FIG. 6. For imaging groups of voxels, superposed images are generated. Of course, while in principle the computer may provide oscillating signals to cause oscillation of the pixels of the LCD at the modulation frequency of 1 GHz, presently known liquid crystals are incapable of excitation at such speeds. Thus, in the embodiment of FIG. 7, the driven LCD does not perform the function of modulation. Upon discovery of new materials capable of such oscillation, however, the same may be used in the embodiment of FIG. 7 to provide both modulation and phase pattern steering of the incoming light rays.

The required optical-carrier light (which may or may not be coherent) may be applied to the plural pixels of the above described zone plate by beam splitting light rays, whether continuous or pulsed, outputted by a laser and properly modulated.

Alternatively, the phased array of modulated coherent light rays may be provided by an array of electro-optic or acousto-optic devices, driven by sinusoidal signals of predetermined phase relationships. The modulators receive input signals oscillating at the modulation frequency, with the predetermined phase distribution determined by the phase pattern to be applied to the light rays. This embodiment provides for both modulation and phase-pattern steering of the coherent light rays.

Yet another contemplated embodiment of the invention utilizes an array of opto-optic devices (e.g., SEED's, self electro-optical devices) for providing the properly phased array of modulated light rays. Such devices, similarly to the above described modulators, are also capable of modulating the light rays in a known manner. This embodiment is particularly useful for miniaturization and for improved resolution. Of course, varying degrees of modulation are effected by the electro-optic or acousto-optic modulators, or by the SEED's, to provide the above described compensation for attenuation of modulation intensity within the tissue.

Still another modification of the invention utilizes bundles of optical fibers of different lengths which form a plurality of delay lines. By passing the coherently modulated light rays through the fibers, and by distributing the fibers in accordance with the pattern shown in FIG. 6, the proper phasing is provided to a plurality of light rays incident on the object to be imaged.

In this embodiment, a single modulator is used to output a modulated light beam to one of several fibers of different lengths in order to provide a desired amplitude and phase modulation to a particular point of the object. Optical switching may be used to switch the different length fibers to the modulator to provide the different phase pattern to the object.

In another embodiment, free space delay lines may be used to provide outputs from various modulators to the surface of the object. That is, corner cubes having different path lengths therebetween may be placed in an optical path between the outputs of the modulators and the object to provide such free space delay lines. Alternatively, various ones of the light beams may be provided to the surface of the object at different angles of incidence, thus increasing the optical path prior to impacting on the object.

Figure 8:
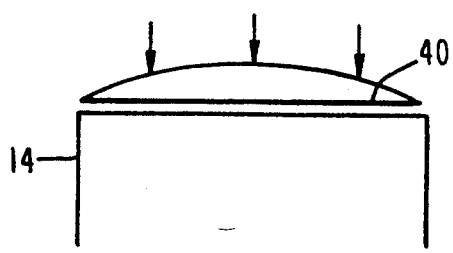
FIG. 8 shows another embodiment of an imaging device in accordance with the invention.

Yet another embodiment, illustrated in FIG. 8, utilizes optical properties of various tissue-like materials to form a diffusive wave lens 40. Specifically, a material such as Delrin ® (acetal copolymer) may be shaped to provide the appropriate delays to the plural light rays, because of the varying thickness of the lens. In such lenses, a balloon structure or other shaped transparent mold may be used, filled with a milky white plastic at varying pressure in order to change the shape thereof.

Figure 9:
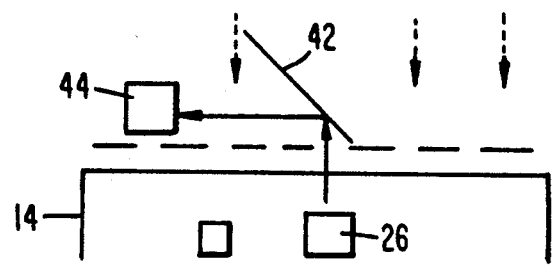
FIG. 9 shows apparatus for receiving reflected light from the imaged voxel.

Preferably, rather than detecting transmitted light, it is contemplated that a device shaped like a Fresnel zone plate be used to provide detection of light reflected by the voxel. Particularly, the open central portion of the zone plate, corresponding to the central portion of the bull's eye pattern of FIG. 6, receives the reflected light from the imaged voxel. By choosing a modulation frequency which results in a requirement for a blocked (non-transmissive) central portion of the plate, a mirror 42 may be placed at the center, as shown in FIG. 9, while a photodetector 44 may be positioned to receive light reflected by mirror 42. Preferably, such a mirror would be semitransparent if extending over a separate grate opening in the zone plate, thus to permit application of modulated light rays (shown by the dashed arrows in FIG. 9) to each of the openings of the ring pattern. Further, the detector 44 is positioned so as not to obstruct any openings of the zone plate. Similar considerations are applicable to the various other phase steering embodiments hereinabove described. Of course, the detector may be located at the opposite side of the object to detect transmitted rays rather than reflected rays.

In accordance with the invention, there has thus been provided a method and apparatus for imaging of an object by interference among an array of differently phased intensity modulated light beams applied to and diffusively propagating through the object. Provision of proper phasing for the incident light rays effectively steers the imaging beam to image a desired voxel within the object by establishing a constructive interference thereat. Provision of a spatial pattern of modulation amplitudes compensates for attenuation of the modulation amplitude by the turbid object. Application of different phasing arrangements, in sequence or in superposition, selects any arbitrarily shaped group of voxels, forming a portion of the object, to be imaged. Where the different phases are provided in sequence there effectively results a non-mechanical scanning of an arbitrarily selected array of voxels within the object. Where the different phases are provided in superposition there results simultaneous acquisition and imaging of data for the selected array of voxels. The incident light rays are modulated at a frequency having a sufficiently long wavelength to assure coherence of the imaging beams throughout the volume of the object. Light rays of different modulation frequencies may be used to provide simultaneous imaging with single voxel resolution. The amplitude of the detected light rays provides an absorption characteristic of the imaged portion for that wavelength. Additional information descriptive of optical density, fluorescence, and other characteristics of the object is obtained from the relative phases of the detected light rays.

The foregoing description of the preferred embodiments of the invention has been presented for purposes of illustration and description. It is not intended to be exhaustive or to limit the invention to the precise forms disclosed since many modifications or variations thereof are possible in light of the above teaching. All such modifications are within the scope of the invention. The embodiments described herein were chosen and described in order best to explain the principles of the invention and its practical application, thereby to enable one of ordinary skill in the art to utilize the invention in various embodiments and with various modifications as are suited to the particular use contemplated therefor. It is intended that the scope of the invention be defined by the claims appended hereto, when interpreted in accordance with full breadth to which they are legally and equitably entitled.

We claim:

1. A method for imaging an object comprising the steps of:
    applying modulated optical rays to the object, the rays each having an amplitude and a phase which are modulated at respective modulating frequencies and relative phaseshifts;
    selecting the relative phaseshifts of the modulated rays to cause constructive interference among the modulated rays at a predetermined voxel thereby selecting said predetermined voxel for imaging;
    diffusively propagating the modulated rays through the object; and
    detecting an amplitude and phase of a light ray resulting from the constructive interference at the selected voxel for imaging a characteristic thereof.

2. A method as recited in claim 1 comprising the further steps of repeating said selecting step for a sequence of predetermined voxels; repeating said propagating step to diffusively propagate modulated rays through the object to said sequence of predetermined voxels; and repeating said detecting step to detect a sequence of rays respectively resulting from a sequence of constructive interferences at said sequence of voxels, thereby scanning a portion of the object for imaging said characteristic thereof.

3. A method as recited in claim 2 wherein said selecting step comprises the steps of:
    using a signal responsive phase shift means for applying said relative phaseshifts to said rays;
    compensating for attenuation of modulation of the diffusively propagating rays by spatially varying modulation amplitudes of the rays; and
    applying computer generated signals to said signal responsive phase shift means thereby providing non-mechanical scanning of said portion of the object.

4. A method as recited in claim 1 wherein:
    said selecting step comprises selecting the relative phaseshifts of the modulated rays to cause constructive interference among resulting modulation wavefronts at a predetermined plurality of voxels thereby selecting for imaging a portion of the object having a predetermined shape formed of said predetermined plurality of voxels; and
    said detecting step comprises detecting light rays resulting from constructive interference at said portion of the object having a predetermined shape.

5. A method as recited in claim 4 wherein said selecting step comprises the steps of:
    using a signal responsive phase shift means for applying said relative phaseshifts to said rays; and
    applying computer generated signals to said signal responsive phase shift means thereby selecting said predetermined plurality of voxels to form said portion having a predetermined shape for simultaneously imaging said plurality of voxels forming said portion.

6. A method as recited in claim 5 wherein said detecting step comprises the steps of: using a single detector cell for detecting amplitudes and phases of a plurality of light rays from said plurality of voxels and outputting a signal representative of an image of said portion as a function of the amplitudes and phases of said plurality of light rays.

7. A method as recited in claim 6 wherein said step of outputting comprises obtaining averages of the amplitudes and phases of said plurality of light rays and outputting said signal representative of the image of said portion as a function of said averages.

8. A method as recited in claim 1 wherein said selecting step comprises the steps of:
    using a signal responsive phase shift means for applying said relative phaseshifts to said rays; and
    applying computer generated signals to said signal responsive phase shift means thereby providing simultaneous imaging of a plurality of voxels of said object.

9. A method as recited in claim 1 wherein said detecting step comprises the steps of: using a single detector cell for detecting amplitude and phase of a light ray from said selected voxel and outputting a signal representative of an image of said voxel as a function of the amplitude and phase of said light ray.

10. A method as recited in claim 1 wherein said applying step comprises the step of:
using a signal responsive modulating means for modulating said rays with said modulating frequencies and relative phaseshifts; and
applying computer generated signals to said signal responsive modulating means for selecting predetermined modulating frequencies in accordance with characteristics of the object and selecting predetermined relative phaseshifts for selecting a predetermined voxel of the object to be imaged.

11. In an imaging apparatus for imaging an object by applying light rays thereto, the improvement comprising:
parameter detecting means for obtaining physical parameters descriptive of a portion of the object, said parameter detecting means including:
phasing means for providing predetermined phases to modulated light rays applied to the object to cause constructive interference between modulation wavefronts at a preselected voxel within the object; and
detecting means for detecting an amplitude and phase of a diffusively propagated light ray resulting from the constructive interference at the selected voxel for imaging a physical parameter descriptive thereof.

12. An improved imaging apparatus as recited in claim 11 wherein said phasing means comprises a signal responsive phase shift means for providing said predetermined phases to said modulated light rays.

13. An improved imaging apparatus as recited in claim 12 wherein said signal responsive phase shift means comprises a signal responsive zone plate.

14. An improved imaging apparatus as recited in claim 13 wherein said signal responsive zone plate comprises LCD means having a plurality of cells, each cell responsive to a signal for controlling a light transmittance characteristic thereof.

15. An improved imaging apparatus as recited in claim 14 further comprising generating means for generating a plurality of signals for controlling said light transmittance characteristic of said plurality of cells thereby to provide said predetermined phases to said modulated light rays and to transmit said modulated light rays to the object.

16. An improved imaging apparatus as recited in claim 12 wherein said signal responsive phase shift means comprises a plurality of signal responsive electro-optic modulating means, each modulating means responsive to a signal for controlling a light transmittance characteristic thereof, and
generating means for generating a plurality of signals for controlling said light transmittance characteristic of said plurality of modulating means thereby to provide said predetermined phases to said modulated light rays and to transmit said modulated light rays to the object.

17. An improved imaging apparatus as recited in claim 12 wherein said signal responsive phase shift means applies a predetermined phase pattern to said light rays for causing constructive interference between the modulation wavefronts at a predetermined plurality of voxels, thereby selecting a predetermined plurality of voxels to form said portion of the object to be imaged.

18. An improved imaging apparatus as recited in claim 17 wherein said detecting means comprises a detector array for simultaneously receiving a plurality of diffusively propagated light rays resulting from the constructive interference at the selected plurality of voxels for simultaneously imaging an absorption characteristic of said plurality of voxels forming said portion of the object being imaged.

19. An improved imaging apparatus as recited in claim 18 wherein said signal responsive phase shift means applies to said light rays a plurality of predetermined phase patterns in a predetermined sequence for causing constructive interference between the modulation wavefronts to occur at a predetermined plurality of voxels in a predetermined sequence, thereby enabling said portion to be imaged with a resolution of one voxel in a non-mechanical sequential scan of the portion by the detector array.

20. An improved imaging apparatus as recited in claim 11 further comprising modulating means for modulating said light rays at a predetermined modulation frequency selected to provide a predetermined resolution of the imaged absorption characteristics.

21. An improved imaging apparatus as recited in claim 11 further comprising means for applying to the object light rays of a plurality of optical frequencies thereby to obtain absorption spectra for said portion of the object.

* * * * *